(12) United States Patent
Rai et al.

(10) Patent No.: US 7,332,600 B2
(45) Date of Patent: Feb. 19, 2008

(54) PROCESS FOR THE PREPARATION OF CRYSTALLINE IMIPENEM

(75) Inventors: Bishwa Prakash Rai, Uttar Pradesh (IN); Neera Tewari, Haryana (IN); Yatendra Kumar, Haryana (IN)

(73) Assignee: Ranbaxy Laboratories Limited, Gurgaon (IN)

( * ) Notice: Subject to any disclaimer, the term of this patent is extended or adjusted under 35 U.S.C. 154(b) by 449 days.

(21) Appl. No.: 10/495,681

(22) PCT Filed: Nov. 18, 2002

(86) PCT No.: PCT/IB02/04804

§ 371 (c)(1),
(2), (4) Date: Aug. 23, 2004

(87) PCT Pub. No.: WO03/042215

PCT Pub. Date: May 22, 2003

(65) Prior Publication Data

US 2005/0004359 A1    Jan. 6, 2005

(30) Foreign Application Priority Data

Nov. 16, 2001  (IN) .................... 1152/DEL/2001

(51) Int. Cl.
*C07D 477/20*  (2006.01)
(52) U.S. Cl. .................................................. 540/350
(58) Field of Classification Search ................. 540/350
See application file for complete search history.

(56) References Cited

U.S. PATENT DOCUMENTS

| 4,194,047 | A | | 3/1980 | Christensen et al. ........ 546/272 |
| 4,260,543 | A | | 4/1981 | Miller ...................... 260/245.2 |
| 4,292,436 | A | | 9/1981 | Liu et al. ..................... 560/148 |
| 5,061,730 | A | * | 10/1991 | Uchida et al. ............... 514/563 |
| 5,124,323 | A | * | 6/1992 | DiNinno et al. ............... 514/80 |
| 5,240,920 | A | * | 8/1993 | DiNinno et al. ....... 514/210.14 |
| 5,321,020 | A | * | 6/1994 | Jasys ...................... 514/210.11 |
| 5,621,084 | A | * | 4/1997 | Honda et al. ............... 536/1.11 |
| 7,071,330 | B2 | * | 7/2006 | Williams et al. ............. 540/350 |
| 2003/0153191 | A1 | * | 8/2003 | Saitoh et al. ................ 438/694 |
| 2004/0176351 | A1 | * | 9/2004 | Cvetovich et al. ...... 514/210.13 |
| 2004/0235817 | A1 | * | 11/2004 | Brands et al. ......... 514/210.13 |
| 2004/0242865 | A1 | * | 12/2004 | Kumar et al. ............... 540/350 |

FOREIGN PATENT DOCUMENTS

| DE | 268 240 | 5/1989 |
| EP | 0 006 639 | 1/1980 |
| EP | 1 096 020 | 5/2001 |
| WO | WO 97/09300 | 3/1997 |
| WO | WO 97/33905 | 9/1997 |
| WO | WO 00/56693 | 9/2000 |
| WO | WO 02/36594 | 5/2002 |
| WO | WO 02/94773 | 11/2002 |

OTHER PUBLICATIONS

Connolly et al., "Freeze Crystallization of Imipenem", *Journal of Pharmaceutical Sciences*, 85(2):174-177 (1996).
Database WPI Week 200015, Dec. 1, 1999, Derwent Publications Ltd., London, GB; AN 2000-161717, XP002233690 & CN 1,236,781 (China Medicine & Biologic Prod.) abstract.
Database CA Online. Chemical Abstracts Service, Columbus, Ohio, US; Bristol-Myers Co., USA: "Crystalline cephalosporin" retrieved from STN Database accession No. 84:184895 XP002233687 abstract & JP 49 126811 (Bristol-Myers Co., USA) Dec. 4, 1974.
Database CA Online. Chemical Abstracts Service, Columbus, OH, US; Gopchak et al: "Production of anhydrous.alpha.-glucose in crystallizers" retrieved from STN Database accession No. 91:75992 XP002233688 abstract & Pishchevaya Promyshlennost, Seriya 5: Krakhmalo-Patochnaya Promyshlennost (Nauchno-Tekhnicheskii Referativnyi Sbornik) (1979), (1), 13-16.
Database CA Online. Chemical Abstracts Service, Columbus, Oh, US; Ootsuka et al: "Purification of 2,6-napthalenedicarboxylic acid dimethyl ester" retrieved from STN Database accession No. 122:55732 XP002233689 abstract & JP 03 256262 A (Petroleum Energy Center Found, Japan;Cosmo Oil Co. Ltd.) Sep. 13, 1994.

* cited by examiner

*Primary Examiner*—Mark L. Berch
(74) *Attorney, Agent, or Firm*—Jayadeep R. Deshmukh, Esq.; George E. Heibel, Esq.

(57) ABSTRACT

The present invention relates to a cost effective and industrially advantageous process for the preparation of imipenem of high purity, which comprises dissolving crude imipenerm in warm water to which some base has been added to obtain a solution, subjecting the resultant solution to activated carbon treatment, and adding an organic solvent to precipitate imipienem monohydrate as a crystalline product.

13 Claims, No Drawings

PROCESS FOR THE PREPARATION OF CRYSTALLINE IMIPENEM

FIELD OF THE INVENTION

The present invention relates to a cost effective and industrially advantageous process for the preparation of imipenem of high purity.

BACKGROUND OF THE INVENTION

Imipenem monohydrate is the N-formimidoyl derivative of thienamycin, and has the structural Formula I

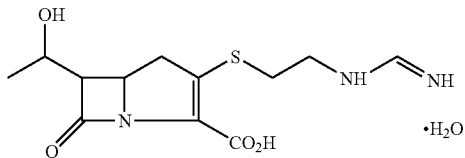

FORMULA I

It is the first clinically available member of new class of β-lactam antibiotics that possess the carbapenem ring system. Imipenem exhibits an extremely broad spectrum of activity against gram-positive and gram-negative aerobic and anaerobic species, which is partly due to its high stability in the presence of β-lactamases.

Imipenem was first disclosed in U.S. Pat. No. 4,194,047 and was obtained by lyophilization technique. The product obtained by lyophilization is found to be largely amorphous and stated to be thermodynamically unstable. The process also involves an initial purification through column chromatography using hydrophobic resins.

A thermodynamically stable crystalline monohydrate form of imipenem is disclosed in U.S. Pat. No. 4,260,543 which is obtained by crystallization of a lyophilized sample of imipenem. However, this process is not satisfactory on a commercial scale as it requires isolation of the product by column chromatography, lyophilization, followed by crystallization. Moreover, the prolonged process for isolation of the final product leads to degradation of imipenem, thus affecting the purity of the product.

U.S. Pat. No. 4,292,436 discloses crystalline imipenem by purifying the crude product by column chromatography. Another method for preparing imipenem having a high degree of crystallinity by freeze crystallization process has been reported by Connolly et. al. in *J. Pharm. Sci*, 85, 174(1996). However, these processes are tedious, cumbersome and unsuitable for industrial use.

Our pending PCT application No. PCT/IB02/01718 provides a process for the isolation of crystalline imipenem monohydrate from a solution containing imipenem without using lyophilization, freeze drying or chromatographic techniques at any stage.

However, it has been observed that imipenem obtained by methods which do not involve column chromatography contains polymeric and colored impurities. The polymeric impurities are side products formed during the synthesis of imipenem, which crystallize out along with imipenem. These impurities do not have any ultra-violet absorption and hence, are difficult to detect. Although, the polymeric impurities are not reflected in the qualitative determination of purity by HPLC, but the quantitative determination (Assay) shows that the product has about 5-10% of these impurities.

The colored impurities are degradation products of imipenem formed during production or under storage, imipenem being inherently unstable in solution as well as sensitive to heat and light. These colored impurities adversely affect the appearance of imipenem, which may appear from pale yellow to brownish powder instead of the desired white crystalline powder.

The purification of imipenem is difficult due to its unstable nature. The crystalline imipenem has relatively low solubility in water at room temperature. A purification process thus requires dissolving imipenem in large volumes of water. The chromatographic purification also requires eluting with large volumes of water. The process of recovering the purified product is uneconomical as it requires concentrating water at low temperature thus necessitating the use of lyophilization, reverse osmosis, or freeze drying techniques.

SUMMARY OF THE INVENTION

It is an object of the present invention to provide a simple, practical and efficient method for the preparation of pure crystalline imipenem monohydrate from crude imipenem containing impurities including polymeric and colored impurities.

The process of the present invention does not use capital intensive techniques of lyophilization or freeze crystallization as well as the time consuming purification process of column chromatography using expensive hydrophobic resins. The present invention thus fulfills the need for a process for the manufacture of imipenem which is convenient to operate on a commercial scale.

Accordingly, the present invention provides a process for the preparation of pure crystalline imipenem monohydrate of Formula I,

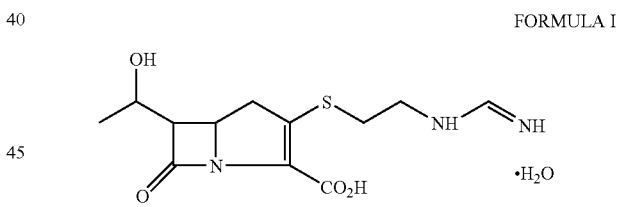

FORMULA I which comprises:
(a) dissolving crude imipenem In water to obtain a solution;
(b) subjecting the resultant solution to activated carbon treatment; and
(c) adding organic solvent to precipitate imipenem monohydrate as a crystalline product.

The crude imipenem can be obtained by any of the methods described in the prior art.

According to one aspect of the present invention, the crude imipenem is dissolved in warm water to which some base has been added and the resulting solution is rapidly cooled to prevent any degradation. The addition of base ensures the stability of imipenem in solution at high temperature by maintaining the pH at about 7.5 to 8.5. Any base known to a person skilled in the art may be used which can bring the pH of the water to about 7.5 to 8.5. Preferably, sodium carbonate is used.

According to the invention, the water is preheated to a temperature of about 35 to 60° C. About 30 to 60 ml of water per 1 g of the crude imipenem is sufficient to achieve the effective purification without any need for concentration/removal of water for isolating the product.

The carbon treatment is carried out at an ambient temperature and at a pH of about 5 to 7 to facilitate the adsorption of impurities. Optionally, sodium bisulfite is added during carbon treatment to obtain good results. The polymeric impurities remain undissolved in water and are filtered out along with carbon.

After carbon treatment, an organic solvent is added to the clear, colorless solution to crystallize out pure imipenem. The crystallization step is preferably carried out at temperatures below 25° C., for example at about 0° C. to about 15° C.

Examples of such organic solvents include lower alcohols such as methanol, ethanol, propanol and isopropanol; ketones such as acetone and methyl ethyl ketone or mixture(s) thereof.

DETAILED DESCRIPTION OF THE INVENTION

In the following section preferred embodiments are described by way of examples to illustrate the process of the invention. However, these are not intended in any way to limit the scope of the present invention.

PREPARATION OF CRYSTALLINE IMIPENEM MONOHYDRATE

EXAMPLE 1

Distilled water (4.0 L) containing sodium bicarbonate (2.6 g) was heated to 45 to 47° C. under nitrogen atmosphere. The crude imipenem (100 g, Assay=90%) was added to the solution, stirred for 2 minutes at 45 to 47° C. and then rapidly cooled to 5 to 10° C. (within 10 to 15 minutes). Activated carbon "Eno Anticromos" (30 g) was added at 20 to 25° C. before cooling the solution to 5 to 10° C. The pH of suspension was adjusted to about 6 with 3N hydrochloric acid and stirred for 45 minutes at 5 to 10° C. under nitrogen. The carbon was filtered and washed with distilled water (500 ml). The flitrate was cooled to 5 to 8° C. and acetone (4.5 L) was added with vigorous stirring maintaining the same temperature. The mixture was further stirred for 2-3 hours at 5 to 10° C. (precipitation of crystalline imipenem monohydrate started within 15 to 20 minutes of acetone addition). Another lot of acetone (2.3 L) was then added and the suspension stirred at 0 to 5° C. for 3-4 hours. The crystalline solid was filtered, washed with acetone and dried under reduced pressure at 40° C. for 3-4 hours to obtain white crystalline imipenem monohydrate (73 g, Assay: 98.5%,).

EXAMPLE 2

The process of Example 1 was repeated using crude crystalline imipenem (100 g, Assay=75%) to obtain white crystalline imipenem monohydrate (65 g, Assay: 98.3%).

EXAMPLE 3

Distilled water (3.0 L) containing sodium bicarbonate (2.6 g) was heated to 48° C. under nitrogen atmosphere. The crude imipenem (100 g, Assay=92%) was added to the solution, stirred for 2 minutes at 48° C. and then cooled to 20 to 25° C. within 5 to 10 minutes. Activated carbon "Eno Anticromos" (20 g) was added to the solution at the same temperature. The pH of suspension was adjusted to about 6 with 3N hydrochloric acid and stirred for 45 minutes at 5 to 10° C. under nitrogen. The carbon was filtered and washed with distilled water (500 ml). Acetone (3.5 L) was added to the filtrate at 5 to 10° C. The mixture was stirred for 3 hours at 5 to 10° C. Another lot of acetone (5.0 L) was then added and the suspension stirred at 0 to 5° C. for 4 hours. The crystalline solid was filtered, washed with acetone and dried under reduced pressure at 40° C. to obtain white crystalline imipenem monohydrate (76 g, Assay: 99.0%).

EXAMPLE 4

The process of Example 3 was repeated using isopropanol instead of acetone during crystallization. The crystalline imipenem monohydrate (71.5 g, Assay: 98.0%) was obtained.

While the present invention has been described in terms of its specific embodiments, certain modifications and equivalents will be apparent to those skilled in the art and are intended to be included within the scope of the present invention.

The invention claimed is:

1. A process for the preparation of crystalline imipenem monohydrate of Formula I

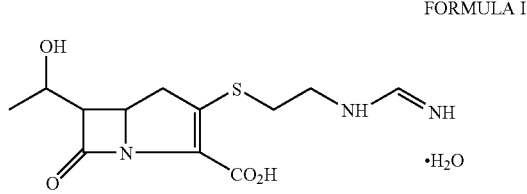

FORMULA I which comprises:
  (a) dissolving crude imipenem in warm water to which some base has been added to obtain a solution;
  (b) subjecting the resultant solution to activated carbon treatment; and
  (c) adding an organic solvent to precipitate imipenem monohydrate as a crystalline product.

2. The process according to claim 1 wherein the crude imipenem is dissolved in water preheated to a temperature of about 35° C. to about 60° C.

3. The process according to claim 2 the base is added to maintain a pH of about 7.5 to 8.5.

4. The process according to claim 3 wherein the base is sodium bicarbonate.

5. The process according to claim 1 wherein the amount of water is about 30 to 60 ml per 1 g of crude imipenem.

6. The process according to claim 1 wherein the carbon treatment is carried out at an ambient temperature.

7. The process according to claim 1 wherein the carbon treatment is carried out at a pH of about 5 to 7.

8. The process according to claim 1 wherein the carbon treatment is carried out in the presence of sodium bisulfite.

9. The process according to claim 1 wherein the organic solvent comprises a lower alcohol, a ketone, and mixture(s) thereof.

10. The process according to claim 9 wherein the lower alcohol is selected from the group consisting of methanol, ethanol, propanol, isopropanol, and mixture(s) thereof.

11. The process according to claim 9 wherein the ketone is acetone, methyl ethyl ketone and a mixture thereof.

12. The process according to claim 1 wherein the crystallization is carried out at a temperature below 25° C.

13. The process according to claim 12 wherein the temperature is from about 0° C. to about 15° C.

* * * * *

UNITED STATES PATENT AND TRADEMARK OFFICE
CERTIFICATE OF CORRECTION

| | | |
|---|---|---|
| PATENT NO. | : 7,332,600 B2 | Page 1 of 1 |
| APPLICATION NO. | : 10/495681 | |
| DATED | : February 19, 2008 | |
| INVENTOR(S) | : Rai et al. | |

It is certified that error appears in the above-identified patent and that said Letters Patent is hereby corrected as shown below:

Title Page, Item [57] Abstract, Line 47 - "imipenerm" should read --imipenem--
Title Page, Item [57] Abstract, Line 51 - "imipienem" should read --imipenem--

In "OTHER PUBLICATIONS"

Item [56] Database CA Online. Chemical Abstracts Service, Columbis, Ohio, US; Bristol-Myers Co., USA: "Crystalline cephalosporin" retreived from STN Database assession No. 84: 184895 XP002233687 abstract & JP 49 126811 (Bristol-Myers Co., USA) Dec. 4, 1974.

"retreived" should read --retrieved--

Database CA Online. Chemical Abstracts Service, Columbus, Oh, US; Ootsuka et al: "Purification of 2,6-napthalenedicarboxylic acid dimehty ester" retreived from STN Database accession No. 122:55732 XP002233768 abstract & JP 03 256262 A (Petroleum Energy Center Found, Japan; Cosmo Oil Co. Ltd.) Sep. 13, 1994

"retreived" should read --retrieved--

Column 2, Line 51 - "In" should read --in--
Column 3, Line 45 - "flitrate" should read --filtrate--

Signed and Sealed this

Twenty-fourth Day of June, 2008

JON W. DUDAS
*Director of the United States Patent and Trademark Office*